United States Patent
Whalen

(10) Patent No.: US 11,081,231 B1
(45) Date of Patent: Aug. 3, 2021

(54) SYSTEM AND COMPUTER IMPLEMENTED METHOD FOR AUTOMATICALLY PROVIDING A SET OF PROCEDURES

(71) Applicant: Janice Whalen, Carp (CA)

(72) Inventor: Janice Whalen, Carp (CA)

( * ) Notice: Subject to any disclaimer, the term of this patent is extended or adjusted under 35 U.S.C. 154(b) by 0 days.

(21) Appl. No.: 17/235,106

(22) Filed: Apr. 20, 2021

Related U.S. Application Data

(60) Provisional application No. 63/123,752, filed on Dec. 10, 2020.

(51) Int. Cl.
*G08B 23/00* (2006.01)
*G16H 40/20* (2018.01)
*G16H 20/40* (2018.01)

(52) U.S. Cl.
CPC .............. *G16H 40/20* (2018.01); *G16H 20/40* (2018.01)

(58) Field of Classification Search
CPC ...... G16H 40/20; G16H 20/40; G06F 19/363; G06F 19/327
See application file for complete search history.

(56) References Cited

U.S. PATENT DOCUMENTS

| | | | | |
|---|---|---|---|---|
| 2014/0244280 A1* | 8/2014 | Fitz | ................... | G06F 19/00 705/2 |
| 2015/0019252 A1* | 1/2015 | Dawson | ................ | G06Q 10/10 705/3 |
| 2015/0317703 A1* | 11/2015 | Kharraz Tavakol | ... | G16H 40/20 705/2 |

* cited by examiner

*Primary Examiner* — Toan N Pham
(74) *Attorney, Agent, or Firm* — Teitelbaum & Bouevitch; Neil Teitelbaum

(57) ABSTRACT

A computer implemented optimization method automatically provides a set of dental procedures to be performed during a scheduled appointment. A processor determines, from the first plurality of dental procedures, a first list of dental procedures that are to be performed for a first patient during the scheduled appointment. The processor also generates a second list of additional dental procedures that are available to be optionally performed for the same first patient during the same scheduled appointment, and ranks the additional dental procedures based on at least one criterion. The processor automatically generates from the first list and from the second list an appointment set of procedures to optimize the billing value of the scheduled first appointment.

20 Claims, 17 Drawing Sheets

| 1,2,5 | 3,4 | Notes | Treatment Manager | | | | |
|---|---|---|---|---|---|---|---|
| | 08:00a | | D | SMITH Jeanette rc | → | 102a | |
| | 08:15a | | | | | | Close |
| | 08:30a | | | | | | Setup |
| | 08:45a | | D | WATSON Norma rc | → | 102b | Search |
| | 09:00a | | | | | | Next |
| | 09:15a | | | | | | Today |
| | 09:30a | | D | GOERTSEN Susan rc | → | 102c | ☒ Day |
| | 09:45a | | | | | | ☒ Week |
| | 10:00a | | | | | | ☒ Month |
| | 10:15a | | D | HARRIS Lynda rc | → | 102d | 30/OCT/20 |
| | 10:30a | | | | | | |
| | 10:45a | | | | | | |
| | 11:00a | | D | JONES Lenny rc | → | 102e | |
| | 11:15a | | | | | | |
| | 11:30a | | | | | | |
| | 11:45a | | D | LUNCH | → | 104 | |
| | 12:00p | | | | | | |
| | 01:00p | | | | | | |
| | 01:15p | | D | BARNEY Joseph rc | → | 102f | |
| | 01:30p | | | | | | |
| | 01:45p | | | | | | |
| | 02:00p | | D | CURRIE Julie rc | → | 102g | |
| | 02:15p | | | | | | |
| | 02:30p | | | | | | |
| | 02:45p | | | | | | |
| | 03:00p | | | | | | |

| | Personal | Insurance | Treatment | Financial | Appts | Notes | Documents | Meds | | |
|---|---|---|---|---|---|---|---|---|---|---|
| Insurance Company | | | | | Dentist: T | | | | Age: 48 | |
| Date | Type Code | Units | Tooth | Pvdr. | Resp. | Charge | Ins. | Pat. Pays | | |
| 19/JUL/04 | 23321 U | | 47 | T | T | 88.29 | 88.29 | 0.00 | | |
| 07/DEC/04 | 01103 U | | | M | T | 112.58 | 112.58 | 0.00 | | |
| 07/DEC/04 | 11107 U | | | M | T | 16.49 | 16.49 | 0.00 | | |
| 03/DEC/19 | 01202 U | | | M | T | 25.22 | 25.22 | 0.00 | | |
| 03/DEC/19 | 11112 U | | | M | T | 94.18 | 94.18 | 0.00 | | |
| 24/MAY/20 | 11101 U | | | M | T | 32.96 | 32.96 | 0.00 | | |
| 24/MAY/20 | 01202 U | | | M | T | 35.00 | 35.00 | 0.00 | | |
| 24/MAY/20 | 02144 U | | | M | T | 47.00 | 47.00 | 0.00 | | |
| 24/MAY/20 | 12113 U | | | M | T | 29.00 | 29.00 | 0.00 | | |
| 24/MAY/20 | 11107 U | | | M | T | 25.00 | 25.00 | 0.00 | | |
| 24/MAY/20 | 00001 U | | | M | T | 0.00 | 0.00 | 0.00 | | |
| 24/MAY/20 | 01202 U | | | M | T | 35.00 | 35.00 | 0.00 | | |
| 24/MAY/20 | 02144 U | | | M | T | 47.00 | 47.00 | 0.00 | | |
| 24/MAY/20 | 12113 U | | | M | T | 29.00 | 29.00 | 0.00 | | |
| 24/MAY/20 | 11107 U | | | M | T | 25.00 | 25.00 | 0.00 | | |
| 24/MAY/20 | 11112 U | | | M | T | 114.00 | 114.00 | 0.00 | | |
| 24/MAY/20 | 11117 U | | | M | T | 29.00 | 29.00 | 0.00 | | |
| 27/JUN/20 | 00002 U | | | M | T | 160.00 | 160.00 | 0.00 | | |

202 (brace around most rows), 204 (brace around 12113 row)

SMITH, Mrs. Jeanette
Age: 48 Gender: F
Portal: NOT REGISTERED

Contact:
H: (905)387-5767
W: (905)333-1234
O: (905)579-1551
E:

Best Time: Afternoon
Dentist: T Hygienist: M
Last Recall: 24/May/20
Appts: 1
Fri 30/Oct/20 08:00a
Contacts:
Financial:

| | Acct. | Insurance |
|---|---|---|
| Current: | 0.00 | 0.00 |
| 30-59: | 0.00 | 0.00 |
| 60-89: | 0.00 | 0.00 |
| 90+: | 27.20 | 1043.43 |
| Total: | 27.20 | 1043.43 |

Date: 27/JUN/20  Type: Normal  Service Provider: T - Dr. Terry Ackerman  Responsible Provider: T - Dr. Terry Ackerman
Group: exo - Extraction  Units: —  Tooth: 16  Surface: —  Code: 71101 - Uncomplicated Single Tooth
Charge: 160.00  Patient Pays: 0.00  Insurance Company: 160.00  Info
Type Codes:  Save Item

SYSTEM AND COMPUTER IMPLEMENTED METHOD FOR AUTOMATICALLY PROVIDING A SET OF PROCEDURES

CROSS REFERENCE TO RELATED APPLICATIONS

This application claims the benefit of U.S. Provisional Application No. 63/123,752, filed Dec. 10, 2020, the entire contents of which are incorporated herein by reference.

FIELD OF THE INVENTION

The present disclosure relates to the field of dental practice, and more particularly to a system and computer implemented method for automatically providing a dental practitioner with a set of procedures to be performed.

BACKGROUND

In a typical dental office, blocks of time are scheduled in advance for examining and treating patients. The scheduling is, by its very nature, done prior to the occurrence of the appointments that are being scheduled and it is often the case that a time requirement for each of the appointments is not known at the time the schedule is being generated. This creates a dilemma. If a timeslot created for an appointment is too short, then there may be insufficient time to complete all of the tasks that need to be performed during the appointment. As a result, the appointment may run late and disrupt later-scheduled appointments, or alternatively the patient may not be able receive all of the necessary treatments during the appointment. The patient may then be required to book a second appointment in order to receive the remaining treatments. On the other hand, if the scheduled timeslot for an appointment is too long, there may be an insufficient number of tasks available to fill the entire timeslot. Neither result is desirable, since in both instances the practitioner's time is being used inefficiently and/or the patient is not receiving the necessary care in an optimized fashion. Nevertheless, it is still very common for dental offices to schedule appointments that are too long, in order to ensure that the patient is able to receive the dental care they require.

It is also often the case that additional tasks, which do not directly involve treating patients, must be performed during a block of time that is covered by a schedule, but without an adequate amount of time being allocated for performing such tasks. By way of a specific and non-limiting example, a dentist office may create a daily schedule that runs from 8:00 a.m. to 5:00 p.m. with an hour break for lunch. In a typical dentist office, a dental hygienist is permitted up to fifteen minutes of set up time prior to the arrival of the first patient and an additional fifteen minutes after seeing the last patient to clean-up and close the office. Typical setup requirements include changing into uniform after arriving at the dental office in order to comply with requirements that have been imposed during the COVID-19 pandemic, reviewing patient charts, opening the examination room, purging air and water lines, checking step wedges and performing X-Ray maintenance, etc. The first patient can be seated only after the setup tasks have been completed, which imposes a very tight timeframe.

Importantly, certain of these additional tasks cannot be omitted including all personal protective equipment (PPE) requirements, performing COVID-19 symptom pre-screening for each patient, performing a COVID-19 rinse for each patient, etc. The unfortunate result is that the time spent reviewing patient chart information may be reduced, or even nearly eliminated beyond a quick review to avoid putting the patient or the dentist at risk. For instance, the chart information review may be limited to checking for an indication that the patient takes pre-medication prior to any dental appointment and confirming that the medication has been called in and taken by the patient. A quick review may also include checking to see if the patient takes any other medications, has any allergies, etc.

It would be beneficial to provide a system and method that overcomes at least some of the above-mentioned disadvantages and/or limitations.

SUMMARY OF THE INVENTION

In accordance with an aspect of at least one embodiment, there is provided a computer implemented optimization method for automatically providing a set of dental procedures to be performed by a dental practitioner during a scheduled appointment, comprising: accessing, by at least one processor, data stored in one or more storage devices, the data defining a first plurality of dental procedures, and the data further defining a billing rate associated with each dental procedure and a minimum allowable time associated with each dental procedure, wherein some dental procedures of the first plurality of dental procedures have different billing rates associated therewith; determining, from the first plurality of dental procedures, a first list of dental procedures that are to be performed for a first patient during the scheduled appointment; using the at least one processor, generating a second list of additional dental procedures that are available to be optionally performed for the same first patient during the same scheduled appointment, and ranking the additional dental procedures based on at least one of a monetary value contribution to a billing value of the appointment, a frequency of performing the additional dental procedures determined from profile data for the first patient, or a time-allocation requirement of a dental office limited resource; and using the at least one processor, automatically generating from the first list and from the second list an appointment set of procedures to optimize the billing value of the scheduled first appointment, and providing an output of the appointment set of procedures to the dental practitioner, wherein the appointment set of procedures generated is dependent upon the second list being different than a previous second list generated for the same first patient for a previous scheduled appointment, and wherein at least the minimum allowable time is allotted to each of the dental procedures within the appointment set of procedures.

In accordance with an aspect of at least one embodiment, there is provided a system for automatically providing a dental practitioner with a set of dental procedures to be performed during a scheduled appointment, the system comprising: one or more storage devices having stored therein data defining a first plurality of dental procedures, and the data further defining a billing rate associated with each dental procedure and a minimum allowable time associated with each dental procedure, wherein some dental procedures of the first plurality of dental procedures have different billing rates associated therewith at least one processor in communication with the one or more storage devices, the at least one processor configured to: determine, from the first plurality of dental procedures, a first list of dental procedures that are to be performed for a first patient during the scheduled appointment; generate a second list of additional dental procedures that are available to be optionally performed for the same first patient during the same scheduled appointment, and rank the additional dental procedures based on at least one of a monetary value contribution to a billing value of the appointment, a frequency of performing the additional dental procedures determined from profile data for the first patient, or a time-allocation requirement of a dental office limited resource; and automatically generate from the first list and from the second list an appointment set of procedures to optimize the billing value of the scheduled appointment, and provide an output of the appointment set of procedures to the dental practitioner, wherein the appointment set of procedures generated is dependent upon the second list being different than a previous second list generated for the same first patient for a previous scheduled appointment, and wherein at least the minimum allowable time is allotted to each of the dental procedures within the appointment set of procedures.

In accordance with an aspect of at least one embodiment, there is provided a computer-readable medium storing a plurality of instructions which, when executed by a processor, perform a method for automatically providing a dental practitioner with a set of dental procedures to be performed during a scheduled appointment, the method comprising: accessing, by at least one processor, data stored in one or more storage devices, the data defining a first plurality of dental procedures, and the data further defining a billing rate associated with each dental procedure and a minimum allowable time associated with each dental procedure, wherein some dental procedures of the first plurality of dental procedures have different billing rates associated therewith; determining, from the first plurality of dental procedures, a first list of dental procedures that are to be performed for a first patient during the scheduled appointment; using the at least one processor, generating a second list of additional dental procedures that are available to be optionally performed for the same first patient during the same scheduled first appointment, and ranking the additional dental procedures based on at least one of a monetary value contribution to a billing value of the appointment, a frequency of performing the additional dental procedures determined from profile data for the first patient, or a time-allocation requirement of a dental office limited resource; and using the at least one processor, automatically generating from the first list and from the second list an appointment set of procedures to optimize the billing value of the scheduled appointment, and providing an output of the appointment set of procedures to the dental practitioner, wherein the appointment set of procedures generated is dependent upon the second list being different than a previous second list generated for the same first patient for a previous scheduled appointment, and wherein at least the minimum allowable time is allotted to each of the dental procedures within the appointment set of procedures.

BRIEF DESCRIPTION OF THE DRAWINGS

The instant invention will now be described by way of example only, and with reference to the attached drawings, wherein similar reference numerals denote similar elements throughout the several views, and in which:

FIG. 1 shows a portion of an appointment schedule display window of a prior art system.

FIG. 2 shows a portion of a patient treatment history display window of a prior art system.

FIG. 5 depicts an exemplary clinic-side data form relating to general properties of the dental office.

DETAILED DESCRIPTION OF EMBODIMENTS OF THE INVENTION

Figure 3:
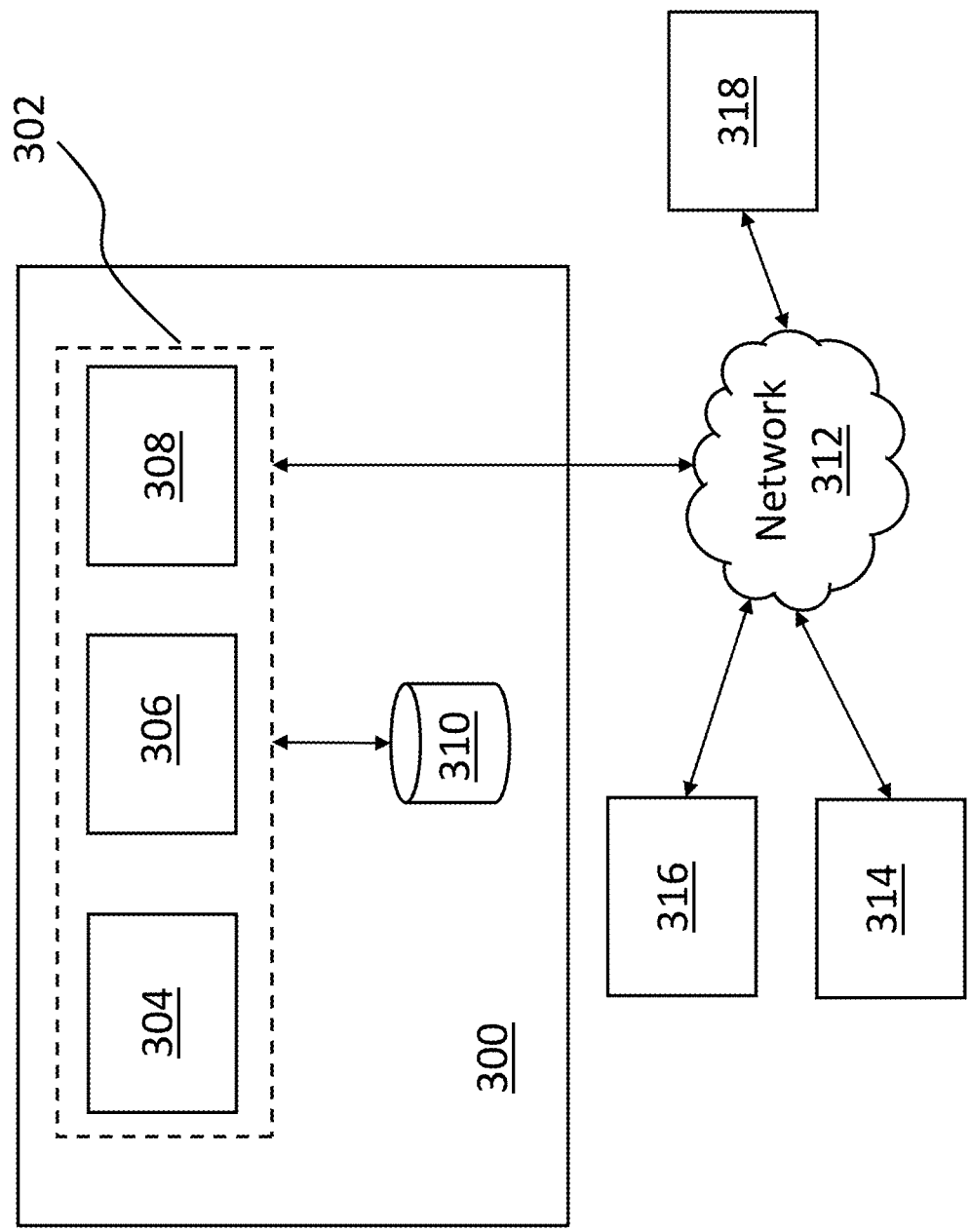
FIG. 3 is a simplified block diagram showing elements of a dental office system according to an embodiment.

The following description is presented to enable a person skilled in the art to make and use the invention and is provided in the context of a particular application and its requirements. Various modifications to the disclosed embodiments will be readily apparent to those skilled in the art, and the general principles defined herein may be applied to other embodiments and applications without departing from the scope of the invention. Thus, the present invention is not intended to be limited to the embodiments disclosed but is to be accorded the widest scope consistent with the principles and features disclosed herein.

In order to distinguish more clearly the various aspects and features of the claimed systems and methods, it is illustrative to begin with a brief discussion of the current systems and methods that are in use, for instance, in dental offices or in other environments in which time-scheduling, task management and productivity are important. The dental office has been selected as a specific example of an environment within which the claimed systems and methods may be beneficially used. In general, dental appointments typically have a scheduled duration within which a plurality of different tasks, some of which are considered "mandatory" and others of which are considered "optional," are to be performed. Of course, other types of environments may also benefit from using the claimed systems and methods, such as for instance other types of medical offices, automobile service centers, business meeting environments, etc.

A prior art system, such as for instance the ABELDent practice management software or the Dentrix dental software, allows a user to gather and analyze data relating to a past treatment history of each patient. In some cases, the prior art system identifies tasks (dental procedures) that have been missed or that are overdue according to an established dental office treatment schedule, which may take into account other information such as for instance insurance coverage limits, etc. Referring to FIG. 1, shown is a portion of an appointment schedule display page 100 of a typical prior art system. The first seven appointments 102a-g, each having an equal one-hour duration, plus a scheduled one-hour lunch break 104, are shown for a particular dental hygienist. As part of their beginning-of-day setup process, the dental hygienist reviews the appointment schedule display page 100 and then, for each one of the scheduled appointments 102a-g, the dental hygienist views a treatment history page associated with the specific patient that will be seen during that appointment. An exemplary treatment history page 200 of the prior art system is shown in FIG. 2. As will be apparent, the treatment history page 200 contains information relating to the dates 202 on which each of a plurality of procedures 204, identified by dental schedule procedure codes, was last performed for the patient, as well as additional information such as for instance insurance and patient payment information.

The dental hygienist determines which tasks (i.e., dental treatments or procedures of the plurality of procedures 204) are available to be performed during the scheduled appointment, taking into account at least the amount of time that is available during the appointment, the past treatment history of the patient and an allowed frequency of repeating each of the treatments, e.g., as defined by dental office policy and/or insurance limits, etc. For instance, dental office policy may specify that a patient is seen every nine months for a recall exam, and that a fluoride treatment is also performed every nine months, but X-Rays are taken only every eighteen months or every 24 months, etc.

This process is repeated for each patient that appears in the appointment schedule display, and may require 2-3 minutes of the dental hygienist's time per patient, or even longer if the dental hygienist is a temporary worker and is unfamiliar with the codes and/or frequency of repeating tasks, or if the most common tasks are not available and a more thorough review of the treatment history is required, etc. In a best-case scenario the total time that is needed to adequately review this type of information for eight or nine patients, which represents a typical workday, is on average at least 16 to 18 minutes. However, the amount of time required could be as much as 30 minutes or more depending on the specific circumstances.

As will be apparent, reviewing patient treatment history alone requires more than the fifteen minutes of time that is allocated to the dental hygienist at the beginning of each day for completing all of the setup tasks, which also includes changing into uniform, purging air and water lines, performing X-Ray maintenance, etc. It will therefore often be the case that the dental hygienist does not have enough time to review all of the patient treatment histories prior to the start of the first scheduled appointment. As a result, the dental hygienist may be forced to review the information for patients that are scheduled later in the day either during their lunch break or during other times when they are not actively treating a patient.

In general, dental hygienist productivity suffers when the full amount of time that is allocated to treat a patient is not being used to actually treat that patient. Often, due to a lack of sufficient time to perform a thorough review of a patient's treatment history, the dental hygienist will fail to select an optimal combination of dental procedures to be performed during each patient's scheduled appointment time during a full workday. This leads to lower dental hygienist productivity, which in turn reduces the dental office's total revenue. Additionally, the allocation of limited resources, such as for instance panoramic X-Ray equipment, may not be optimized and/or may have scheduling conflicts due to a lack of coordination between schedules for different hygienists in the dental office.

One problem associated with the prior art systems is that productivity and other types of optimization is difficult and is at least partially dependent on the skill and knowledge of each dental hygienist. Further, the process of increasing productivity actually involves spending time that could otherwise be used for productive purposes. Another problem associated with the prior art systems is that certain tasks, such as for instance scaling units, are not represented in a way that takes into account all of the components of time that are associated with the task. In the specific example of a scaling unit, the various components of time may include reviewing patient medical history, reviewing patient past dental-treatment history, pre-screening for COVID-19 (or other contagious diseases), administering a COVID-19 rinse, writing up the patient chart, etc. Current systems therefore do not allow for a number of essential and/or mandatory tasks to be tracked and incorporated into the hygienist's treatment plan for each scheduled appointment.

What is missing from the prior art systems is the ability to automatically optimize the dental hygienist's productivity for an appointment that has already been scheduled, such that an optimized combination of tasks is selected to fit within the time that has been scheduled for that patient whist also allowing sufficient time to perform the various tasks that are considered mandatory or that are otherwise not optional.

Referring now to FIG. 3, shown is a simplified block diagram of a dental office system according to an embodiment. The dental office system 300 includes a task management system 302, which includes a plurality of modules or stand-alone applications such as for instance a clinic-side module 304 for managing general properties of the dental office, a hygienist-side module 306 for managing tasks during patient appointments, and a billing module 308 for invoicing and scheduling patient appointments. Optionally, functions of one or more of the modules 304-308 may be combined in different ways. Further optionally, additional modules may be provided for supporting other functions.

The task management system 302 is in communication with data store 310, which may include one or more computer readable storage devices. Also shown in FIG. 3 is a communication network 312, such as a wide area network (WAN) or a local area network (LAN) etc. For instance, network 312 is the Internet. Optionally, data store 310 is partially or entirely cloud based and is accessed via the network 312. Other external systems, including insurance company systems 314, 316 and user systems 318, are illustrated in FIG. 3 and may communicate with the task management system 302 for various reasons.

Figure 4:
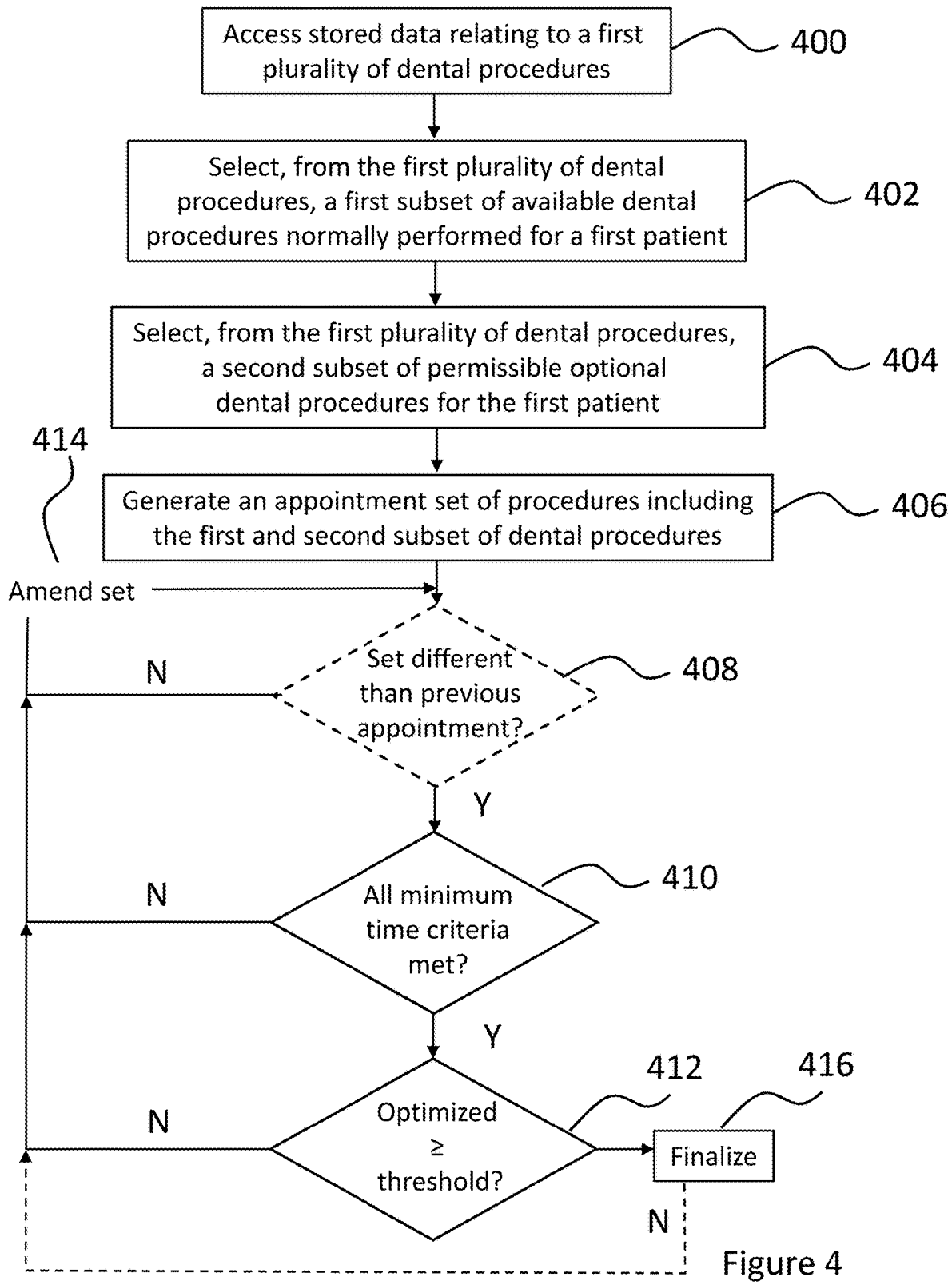
FIG. 4 is a simplified flow diagram of an example process that is suitable for execution on the system of FIG. 3.

Referring now to FIG. 4, shown is a simplified flow chart of a method according to an embodiment. At 400, stored data relating to a first plurality of dental procedures is accessed. For instance, a module such as the hygienist-side module 306 of the task management system 302, which is in execution on at least one processor of a computer system, accesses data stored on the data store 310. The stored data comprises an identification of a plurality of different dental procedures and at least a billing rate and a minimum allowable time associated with each one of the different dental procedures. At least some of the different dental procedures have different billing rates and/or different minimum allowable times associated therewith. Optionally, billing rates may be expressed as a flat rate, a per-unit rate, an hourly rate, etc. or any combination thereof. The stored data may be entered in a manual fashion by a user of the system and may include only those procedures that are performed by a particular dental office. Optionally, the stored data may be provided by a third party as a set of data, and may be updated periodically by the provider of the set of data. For instance, periodic updates may correspond to changes in insurance policy coverage and/or changes to fee schedules created by professional associations.

For a particular first patient, some dental procedures of the first plurality of dental procedures may be available during a current appointment and other dental procedures of the first plurality of dental procedures may not be available during the current appointment. Selection of available dental procedures may be made based on profile data for the first patient, which may be stored in data store 310, and also based on dental office defined treatment intervals etc. For instance, the stored patient profile data may include insurance coverage information defining which ones of the first plurality of dental procedures are covered under the first patient's insurance policy as well as the maximum permitted repetition frequency for the covered dental procedures. The stored profile data may also specify that the first patient will pay for certain dental procedures that are not covered by the insurance policy, which may result in different dental procedures being available for the first patient compared to another patient that is not willing to pay additional amounts.

Only those dental procedures that are determined to be available for the first patient are selectable in the following steps. Optionally, an indication of the available dental procedures is displayed to a user in a human intelligible form. Further optionally, data representing the available dental procedures is transmitted over a communications network. For instance, in a distributed computing implementation, step 400 may be performed in the cloud and the results, in the form of a list of available dental procedures, may be transmitted to the dental office 300 for use in subsequent steps.

At 402 a first subset of dental procedures that is normally performed for the first patient is selected from the available dental procedures of the first plurality of dental procedures. In an implementation, the available dental procedures are displayed to a user in a human intelligible form and the user performs the section by inputting the dental procedures into an electronic form. Alternatively, the system learns the dental procedures that are normally performed for that first patient over time and the selection is done in an automated fashion. By way of a specific and non-limiting example, the first subset of dental procedures may include a recall exam, plus 1.5 units of scaling, plus 1 unit of polishing. These dental procedures are the ones that the first patient expects to receive during every visit to the dentist office.

At 404 a second subset of dental procedures are selected for the first patient from the available dental procedures of the first plurality of dental procedures. The second subset of dental procedures includes dental procedures that are not performed for the first patient during every appointment and/or dental procedures that are performed for the first patient on an irregular basis, such as for instance a full panoramic X-ray or a whitening treatment, etc. In some instances, the second subset of dental procedures may include only one dental procedure or even zero dental procedures. This situation may occur near the end of a calendar year, when the first patient is close to reaching their maximum insurance coverage for the year. In other instances, the second subset of dental procedures may include a plurality of dental procedures, which are ranked by the system according to one or more criteria. For instance, the second subset of dental procedures may be ranked based on a monetary value contribution to a billing value of the appointment. The monetary value contribution may be expressed e.g., in terms of an absolute billing amount associated with each procedure or based on a billing amount per unit of time, or some combination thereof. Alternatively, or additionally, the second subset of dental procedures may be ranked based on a frequency of performing the additional dental procedures as determined from profile data for the first patient. For instance, if it is determined that the first patient is overdue for a procedure, then that procedure may be ranked higher than another procedure that has a higher billing value but that has also been performed more recently for the first patient. Further alternatively, or further additionally, the second subset of dental procedures may be ranked based on a time-allocation requirement of a dental office limited resource, such as for instance panoramic X-ray equipment. In this last example, a procedure that requires the use of the dental office limited resource may be assigned a higher or lower ranking, depending on whether or not there is a potential conflict with a scheduled appointment for a different patient. Different combinations of the above-mentioned ranking criteria may also be utilized.

At 406, an appointment set of procedures is generated for the first patient. The appointment set of procedures is a list of dental procedures to be performed for the first patient during the scheduled appointment and includes all dental procedures of the first subset of dental procedures and at least some dental procedures of the second subset of dental procedures. More particularly, the appointment set of procedures includes specific dental procedures of the second subset of dental procedures that are selected based on the ranking assigned thereto at step 404. Initially, the appointment set of procedures may include more dental procedures selected from the second subset of dental procedures than can be accommodated within the scheduled appointment time. The initial appointment set of procedures may then subsequently be edited to fit within the appointment. Alternatively, the initial appointment set of procedures may be presented to the dental hygienist and the dental hygienist performs the listed procedures in ranked order until the appointment time is completely or nearly completely used up. The hygienist may skip down to lower ranked dental procedures that have a lower minimum allowable time if there is insufficient time remaining during the appointment to complete a higher ranked dental procedure. By providing an extended list of dental procedures, the hygienist has flexibility to quickly adjust the treatment plan for the first patient, e.g., if some of the selected dental procedures take longer than expected or if an unexpected delay occurs.

At optional decision step 408 it is determined if the appointment set of procedures for the current appointment is different than the appointment set of procedures for the first patient's previous appointment. This optional step, when performed, ensures that the patient receives different treatments and procedures over time so that aspects of the first patient's dental health are not overlooked. Optionally, identical appointment sets of procedures may be permitted for two consecutive appointments, but not for three consecutive appointments, etc. Further optionally, some known criteria must be satisfied at decision step 408 to ensure that the first patient's dental health needs are being met and that the differences over time are not merely superficial. For instance, different procedures of the first plurality of dental procedures may be assigned to different groups, such that merely switching one procedure for another procedure within the same group is insufficient to satisfy step 408. In this example, different appointments are considered to be sufficiently different only if a substitution is made between different groups.

If the criteria for decision step 408 is satisfied, or if decision step 408 is not performed, then the process moves to decision step 410 where it is determined if all minimum time criteria are met. In other words, it is determined at step 410 whether or not each separate dental procedure has been allocated an amount of time that is at least as long as the minimum time stored in association with the respective task in the data store 310. Based on profile information for the first patient, the process may allocate more than the minimum time for certain dental procedures. For instance, the profile information may indicate that flossing the first patient's teeth requires additional time because the first patient has tight contacts and/or has very sensitive teeth and/or requests more frequent rinsing, etc.

If the criteria for decision step 410 is satisfied, then the process moves to decision step 412 where it is determined if the appointment set of procedures is optimized at or above a predetermined threshold criterion. For instance, the billing rate that is stored in association with each of the dental procedures of the appointment set of procedures is summed and the total billing value of the appointment is compared to a target billing value. The target billing value may be specific to the user of the system, such as for instance a dental hygienist employed by the dental office, or may reflect the target billing value for the dental office overall, etc. Alternatively, a different criterion may be used to determine whether or not the appointment set of procedures is optimized. By way of an example, some of the selected dental procedures may have an associated billing rate that is low compared to a deemed value of excess time that could be added to an adjacent appointment to allow a higher value procedure to be performed, in which case decision step 412 is partly based on information relating to the adjacent appointment.

Step 412 optionally further includes verifying that the total time allocated for the procedures of the appointment set of procedures matches the total time allocated for the scheduled appointment to within a known threshold tolerance. For instance, step 412 may be satisfied only if the total time allocated for the procedures is within +/−5 minutes of the total time allocated for the appointment, or is within +/−2 minutes, or is within +/−0 minutes, or only if the total time allocated for the procedures is less than the total time allocated for the appointment, etc. When such a criterion has been specified, the appointment set of procedures is not considered to be optimized unless all of the procedures can be performed for the first patient within the time that is available during the appointment.

Referring still to FIG. 4, if the criteria for any one of decision steps 408 to 412 is not satisfied, then the process moves to step 414, and the appointment set of procedures is amended. For example, if it is determined at decision step 408 that the appointment set of procedures for the current appointment and the appointment set of procedures for the first patient's previous appointment are not sufficiently different, then one of the dental procedures is removed from the appointment set of procedures and is replaced by another dental procedure selected from a different group. Steps 408 to 414 may be performed in a fully automated fashion or, alternatively, in a partially automated manner. For instance, step 414 optionally includes receiving input from a user indicating selection of a dental procedure to be removed or substituted in the appointment set of procedures. The input may reflect information provided to the user by the first patient prior to or during the appointment time, such as for instance unusual inflammation or pain that is not otherwise reflected in the patient profile information.

Once the criteria for decision steps 408 to 412 have all been satisfied, then the appointment set of procedures may be finalized at step 416. In one implementation, step 416 is performed automatically, and the user is simply provided with a finalized list of procedures that are to be performed for the first patient during the appointment. In another implementation, step 416 includes displaying the appointment set of procedures to the user in a human intelligible form. The user reviews the displayed appointment set of procedures and finalizes the appointment if the appointment set of procedures is acceptable. Optionally, the user may further amend the appointment set of procedures at step 414 prior to finalizing, in which case an alert is displayed to the user if the proposed amendments fail to meet the criteria that have been established for steps 408 to 412. In response to an alert, the user may make the adjustments that are necessary to ensure that all criteria at steps 408 to 412 are satisfied, or the user may override the alert and finalize the appointment. Alternatively, an automated optimization is performed based on the appointment set of procedures as amended by the user to obtain an updated appointment set of procedures to be finalized.

Additional features of the dental office system 300 will now be discussed in greater detail. For ease of understanding, the clinic-side module 304 and the hygienist-side module 306 are treated as separate modules in the following discussion. However, one of ordinary skill in the art will appreciate that the clinic-side module 304 and the hygienist-side module 306 may be combined into a single module or implemented using additional sub-modules, etc.

Figure 5:
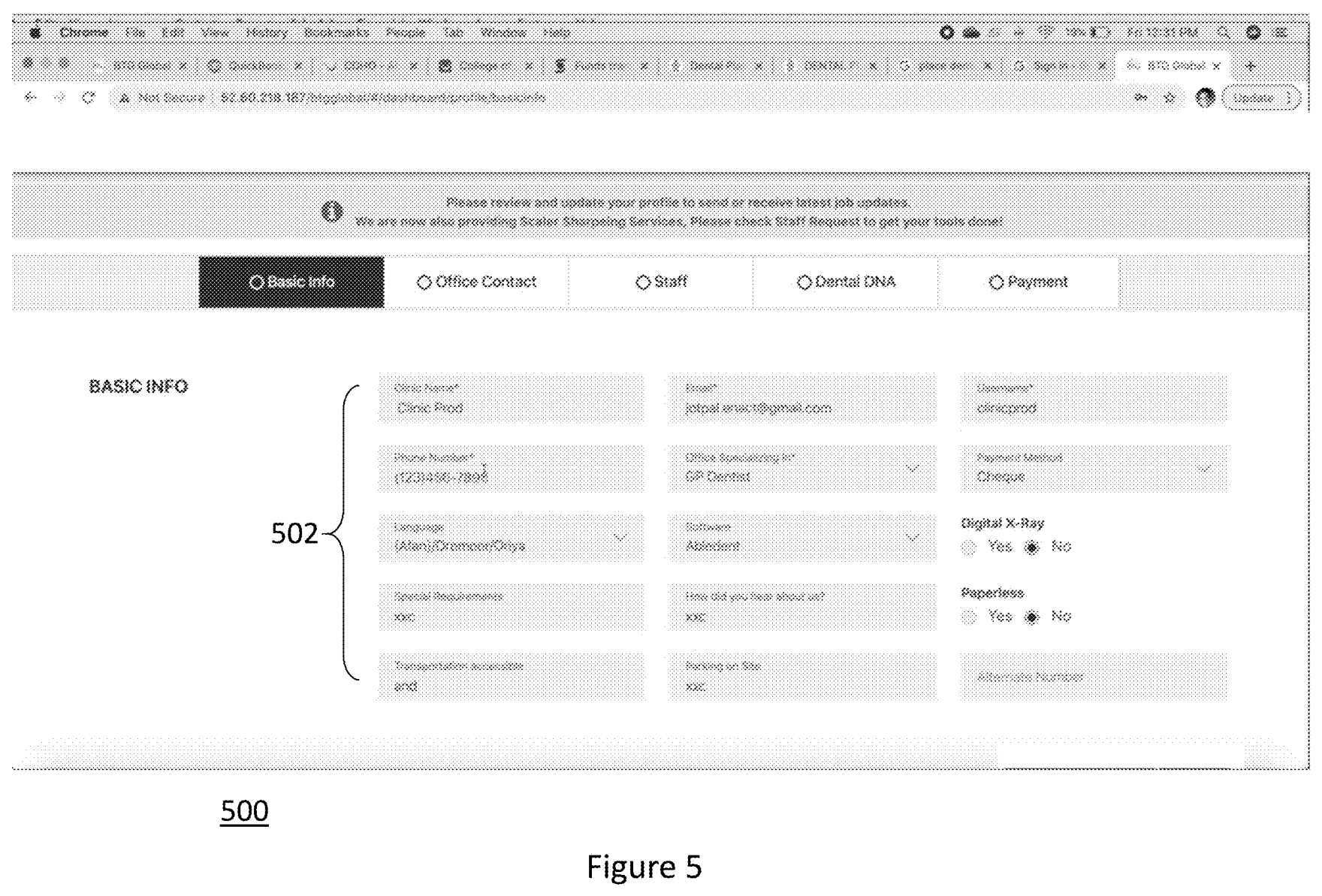

FIG. 5 depicts an exemplary clinic-side data form 500, relating to general properties of the dental office. The form 500 shown in FIG. 5 includes a summary 502 of basic contact information for the dental office, specialization, accessibility, type of software used, type of X-Ray equipment, etc. The information shown in form 500 may be entered when the dental office system is initially set up and then updated by a user as the dental office properties change over time.

Figure 6:
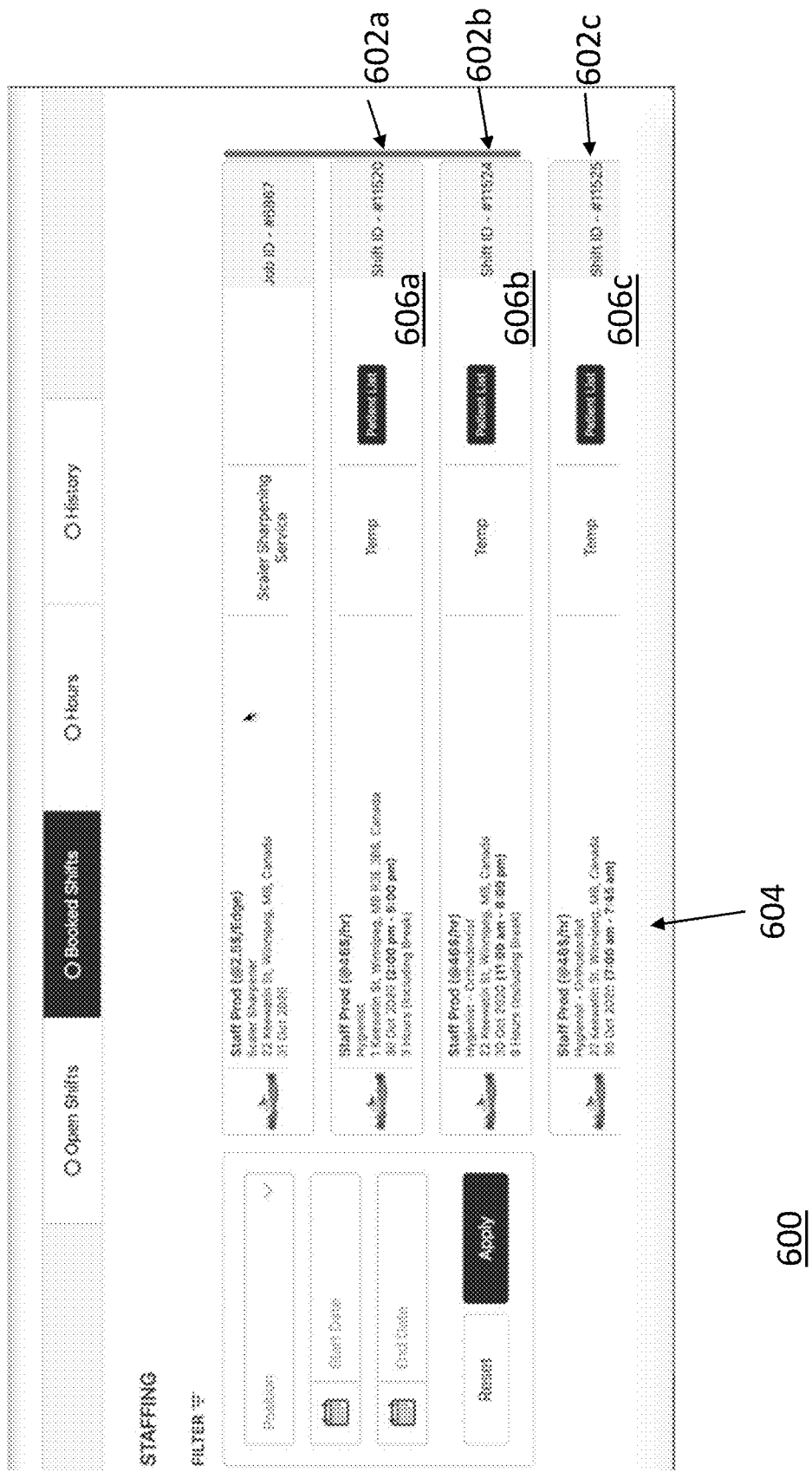
FIG. 6 depicts an exemplary clinic-side data form relating to a plurality of booked dental hygienist shifts.

FIG. 6 depicts an exemplary clinic-side data form 600, relating to a plurality of booked dental hygienist shifts 602*a-c* identified by shift reference number. The displayed information includes fields shown generally at 604, which contain inter alia an indicator of the different hygienists' identities, scheduled shift information (date/specific hours worked/number of hours in the shift), etc. The displayed information also includes a link 606*a-c* to the patient information corresponding to each one of the shifts 602*a-c*. The information shown in form 600 may be entered on a weekly or bi-weekly basis according to scheduling preferences, and may be updated over time if one hygienist leave or a new hygienist is hired, etc.

Figure 7:
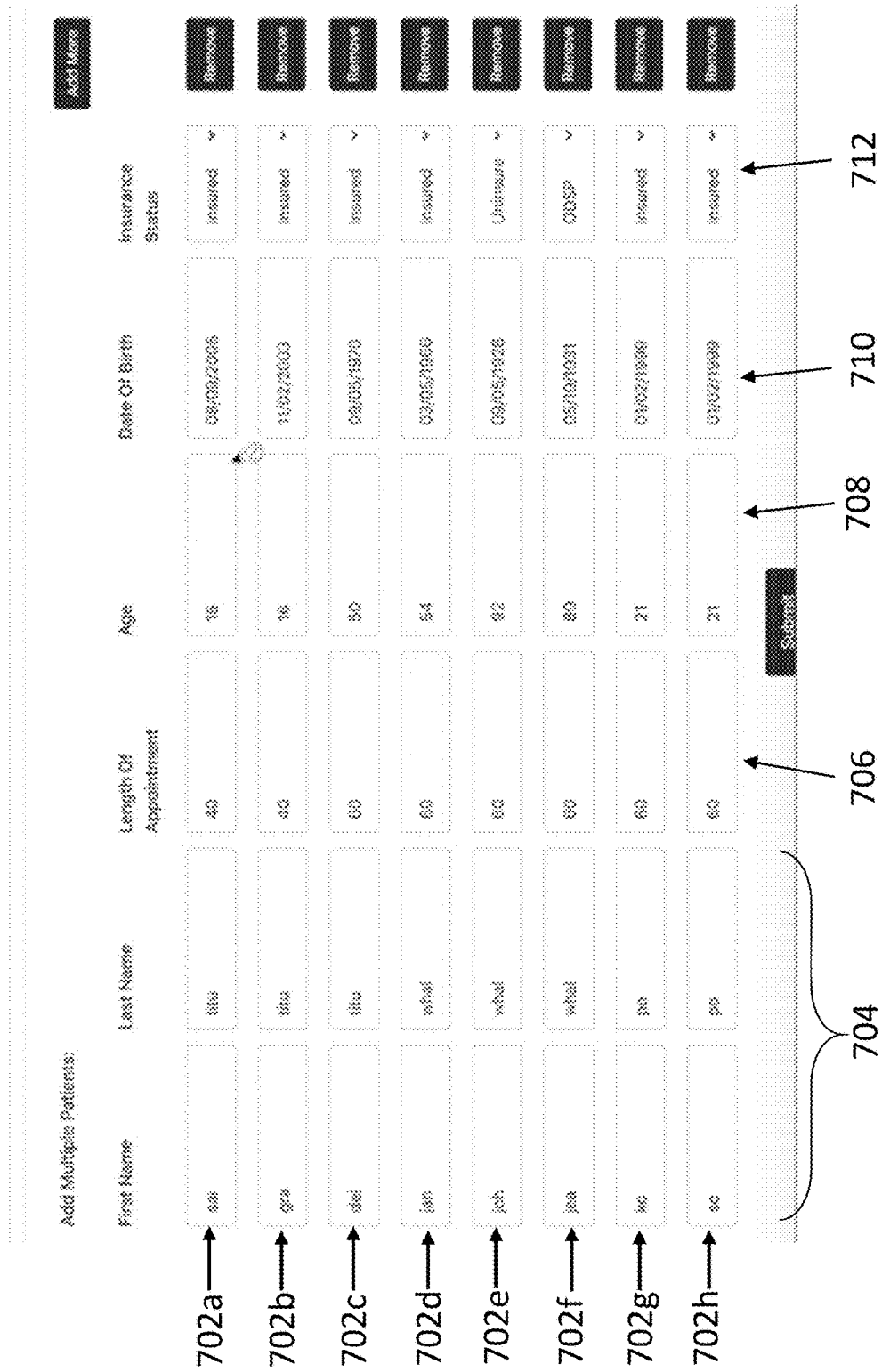
FIG. 7 depicts an exemplary clinic-side data form relating to scheduled appointment patient information.

FIG. 7 depicts an exemplary clinic-side data form 700 relating to patient information for appointments 702*a-h* scheduled during one of the shifts 602*a-c* listed in FIG. 6. The patient information for each one of the appointments 702*a-h* includes e.g., patient identification information 704, e.g., patient first and last names, a scheduled duration 706 of each appointment, an age 708 of each patient calculated automatically based on date of birth information 710, and an insurance status 712 (e.g., insured/uninsured/special insurance status). The information provided using data form 700 may be used to populate the patient profile data that is used in the process that was described with reference to FIG. 4.

Figure 8:
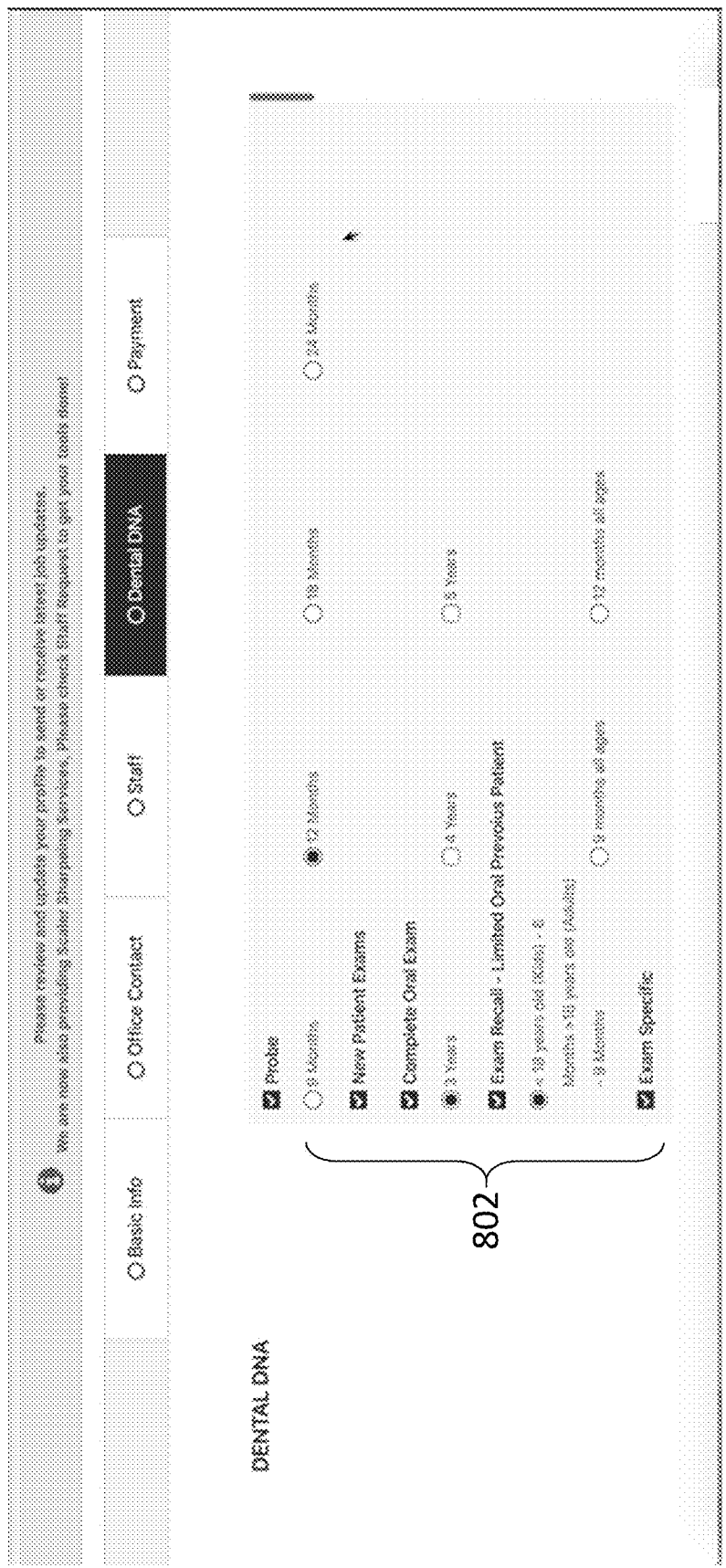
FIGS. 8-10 depict different portions of an exemplary clinic-side data form relating to clinic-defined treatment intervals and related clinic-specific information ("Dental DNA").
Figure 9:
Figure 10:
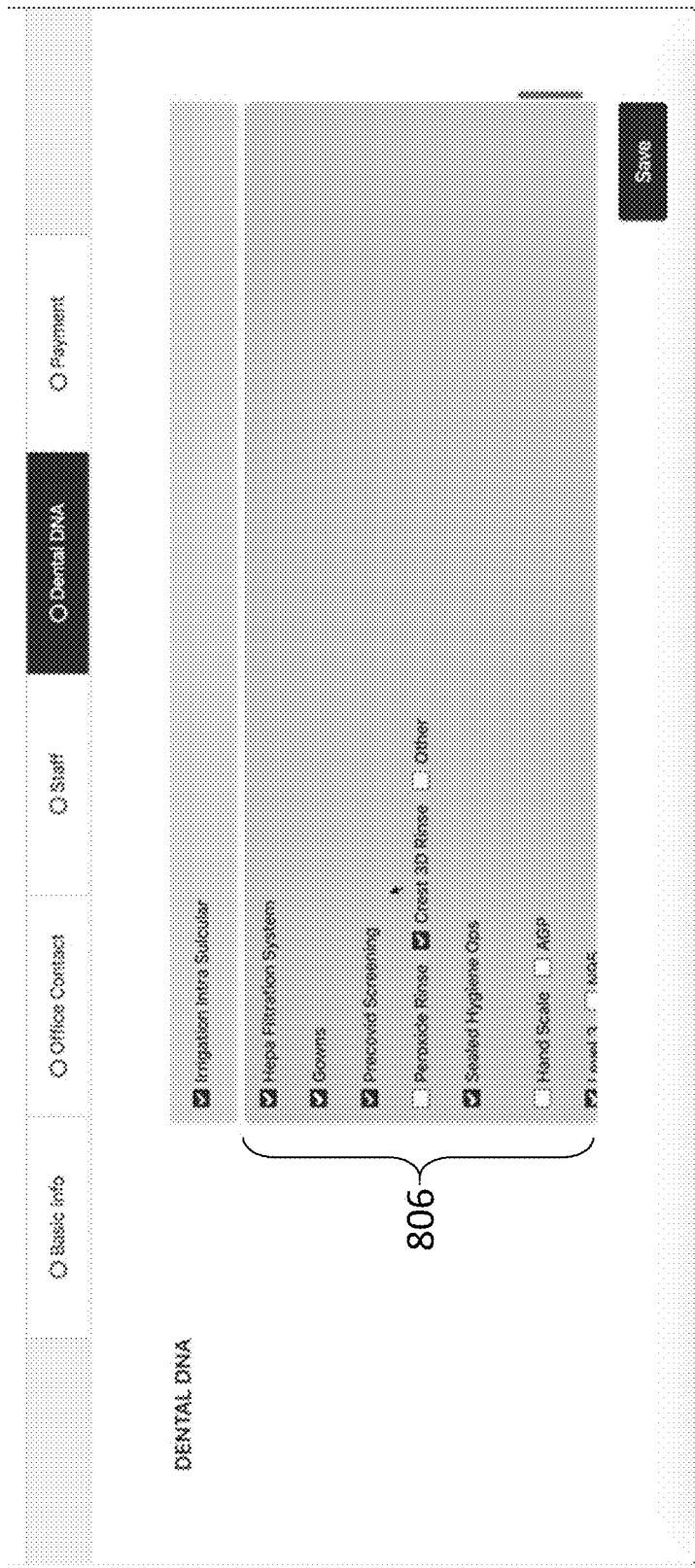

FIGS. 8-10 depict different portions of an exemplary clinic-side data form 800 relating to clinic-defined treatment intervals and related information (Dental DNA). The Dental DNA form is populated e.g., by a user at the dental office when the dental office system is being set up. The Dental DNA information relates to the dental office procedures 802, such as for instance frequency of recall examinations, frequency of fluoride treatment, frequency of obtaining different types of X-Rays films, etc. Some of the information 804 may be associated with different patient age groups, and in particular recall examinations, polishing etc. may have different frequencies for patients under the age of 18 compared to frequencies of patients over the age of 18, etc. The Dental DNA additionally includes other properties 806 unique to the dental office, such as for instance the type of filtration, and other protective measures used during patient appointments. Of course, over time the Dental DNA information 802-806 may be updated if insurance coverage or dental office policies change. The Dental DNA information 802-806 is used during the selection of the specific treatments or procedures that are to be performed for each patient during their respective appointment, as was described with reference to FIG. 4.

Figure 11:
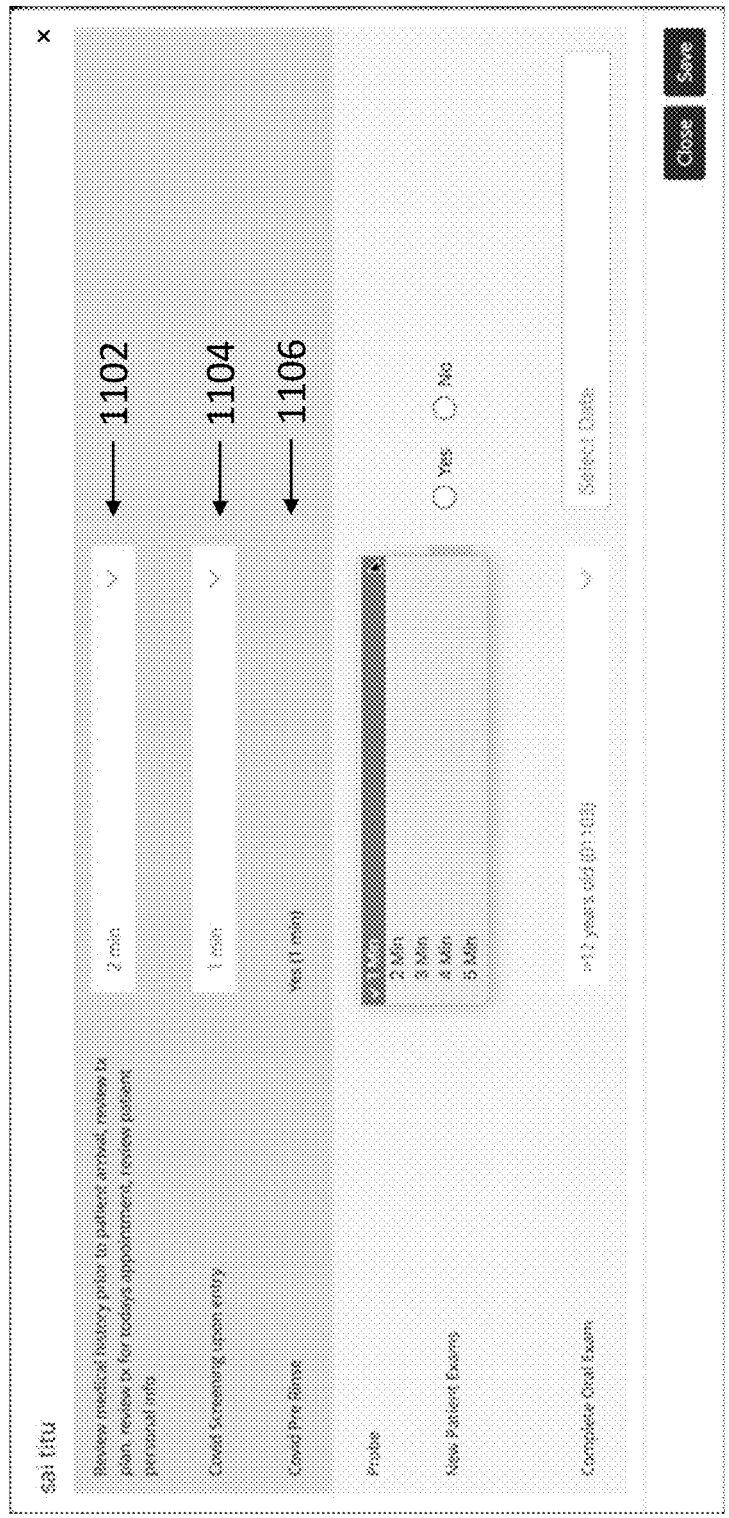
FIGS. 11-13 depict different portions of an exemplary hygienist side data form relating to past treatment information for a first patient.
Figure 12:
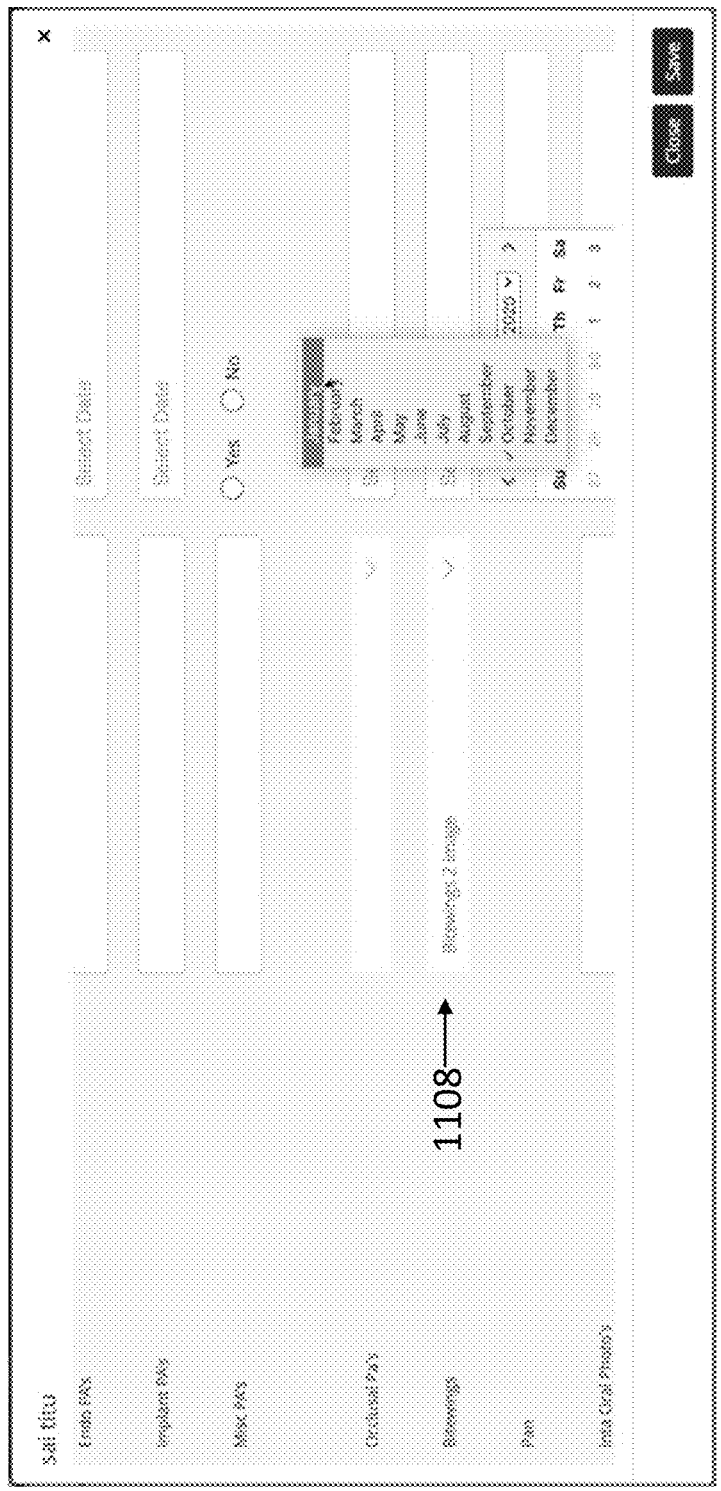
Figure 13:
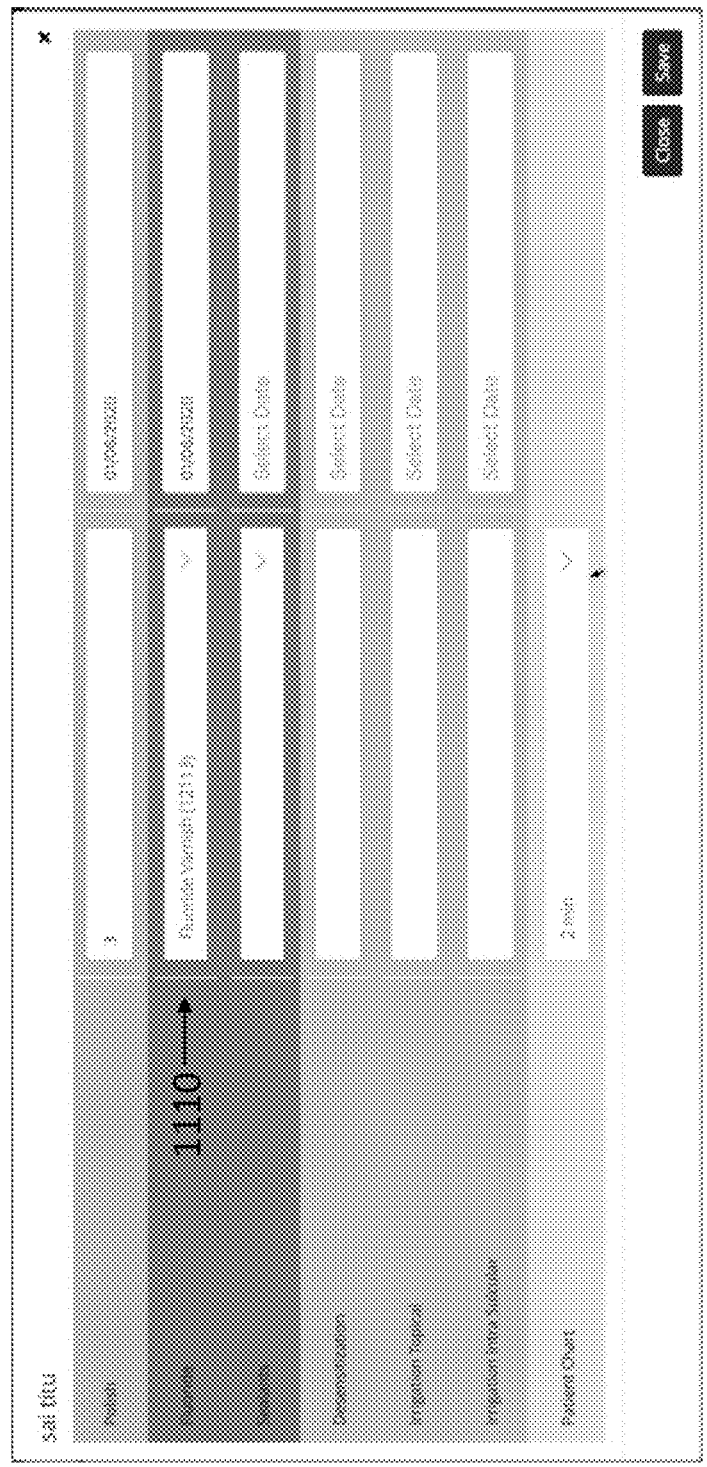

FIGS. 11-13 depict different portions of an exemplary hygienist side data form 1100 for providing treatment history information for a first patient. In particular, the form 1100 shown in FIGS. 11-13 corresponds to the first appointment 702a in the list of appointments shown in FIG. 7 and is shown in a partially populated condition. As depicted in FIGS. 11-13, the dental hygienist has entered values into respective fields of the form, including a first value corresponding to a time 1102 for reviewing patient medical history prior to arrival, a second value corresponding to a time 1104 for COVID screening, a third value corresponding to a time 1106 for performing COVID pre-rinse, etc. The hygienist has also entered information 1108 relating to the date that bitewing X-Rays were obtained, information 1110 relating to the date fluoride varnish was applied, as well as other information not discussed explicitly herein. Optionally, at least some of the above-mentioned information is pre-populated in an automated fashion based on stored prior appointment information, and the dental hygienist merely reviews and/or corrects the pre-populated information. The information provided using data form 1100 may also be used to populate the patient profile data that is used in the process that was described with reference to FIG. 4.

Figure 14:
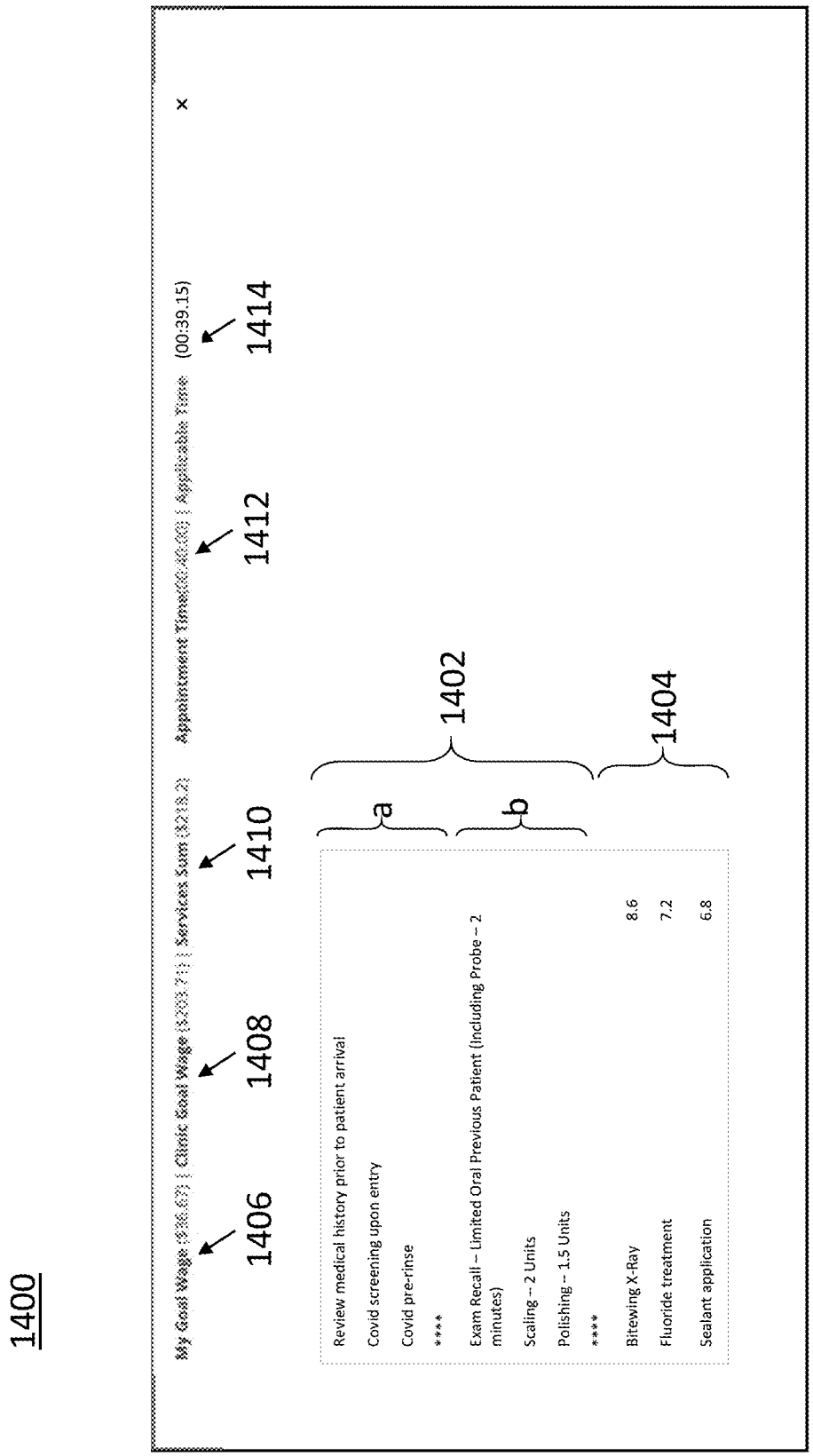
FIG. 14 depicts an exemplary hygienist-side data form for reviewing and/or amending an appointment set of procedures to be performed for the first patient during a scheduled appointment.

FIG. 14 depicts an exemplary hygienist-side data form 1400 for reviewing and/or amending the appointment set of procedures generated according to the process described with reference to FIG. 4. In particular, the form 1400 shown in FIG. 14 corresponds to the first appointment 702a in the list of appointments shown in FIG. 7. The form 1400 displays the dental procedures of the appointment set of procedures including dental procedures of the first subset of dental procedures 1402 and dental procedures of the second subset of dental procedures 1404. For better clarity, the dental procedures of the first subset of dental procedures 1402 are identified in FIG. 14 to denote certain procedures 1402a that are considered "mandatory" and certain procedures 1402b that are normally performed for the first patient but are not considered "mandatory." Further, the dental procedures of the second subset of dental procedures 1404 in this example include a relative ranking value, which is displayed in human intelligible form based on a scale between 0 and 10, wherein a ranking of 10 indicates maximum value based on some known criterion, such as for instance dental office total revenue.

Optionally, form 1400 may display additional information, including e.g., the dental hygienist goal wage 1406, the clinic goal wage 1408 and the services sum 1410 based on the total cost of providing the selected services, etc. The goal wage information 1406 and 1408 is on a per appointment basis, and in the instant example the goal wage values are for the forty-minute time period of the appointment. Alternatively, the goal wages 1406 and 1408 are converted to an hourly basis to facilitate comparisons between appointments of different durations. Also displayed is information relating to the scheduled duration of the appointment ("Appointment Time") 1412 and the time required to perform the selected services ("Applicable Time") 1414. Optionally, other information may be displayed in addition to or in place of the above-mentioned information.

The form 1400 is updated to display the time that is required to perform each treatment or procedure, the fee associated with each treatment or procedure, and the Applicable Time 1414 required to perform all of the selected treatments and procedures. In addition, the Service Sum of the fees for all of the selected treatments and procedures is also updated. Any time remaining after the treatments and procedures have been added to the right side of the form can be added to the scaling time, such that the Applicable Time 1414 plus Scaling Time 1416 is approximately equal to the total Appointment Time. Similarly, if the Applicable Time 1414 for the selected treatments and procedures exceeds the Appointment Time, then the amount of Scaling Time 1416 can be reduced by a corresponding amount.

As noted above, some of the procedures 1402a are considered to be mandatory and must be selected for the appointment. Specific and non-limiting examples of mandatory tasks 1402a include reviewing the medical history, COVID screening, COVID pre-rinse, etc. Other task in addition to or as alternatives to the above-mentioned examples may be mandatory. In general, mandatory tasks 1402a relate to at least one of patient/practitioner safety and administrative/record-keeping. In some embodiments, the mandatory tasks 1402a are automatically added to the appointment set of dental procedures in a non-removable fashion.

Optionally, different appointments for the same or different dental hygienist can be compared to identify potential resource conflicts. For example, if two dental hygienists attempt to finalize overlapping appointments, for different patients, in such a way that creates a potential conflict for usage of a limited resource, such as for instance a panoramic X-Ray, then a warning message may be displayed to one or both of the dental hygienists. The warning message will alert the dental hygienists to either modify the selection of treatments and procedures, or to plan to stagger the panoramic X-Rays to avoid an actual resource conflict.

Figure 15:
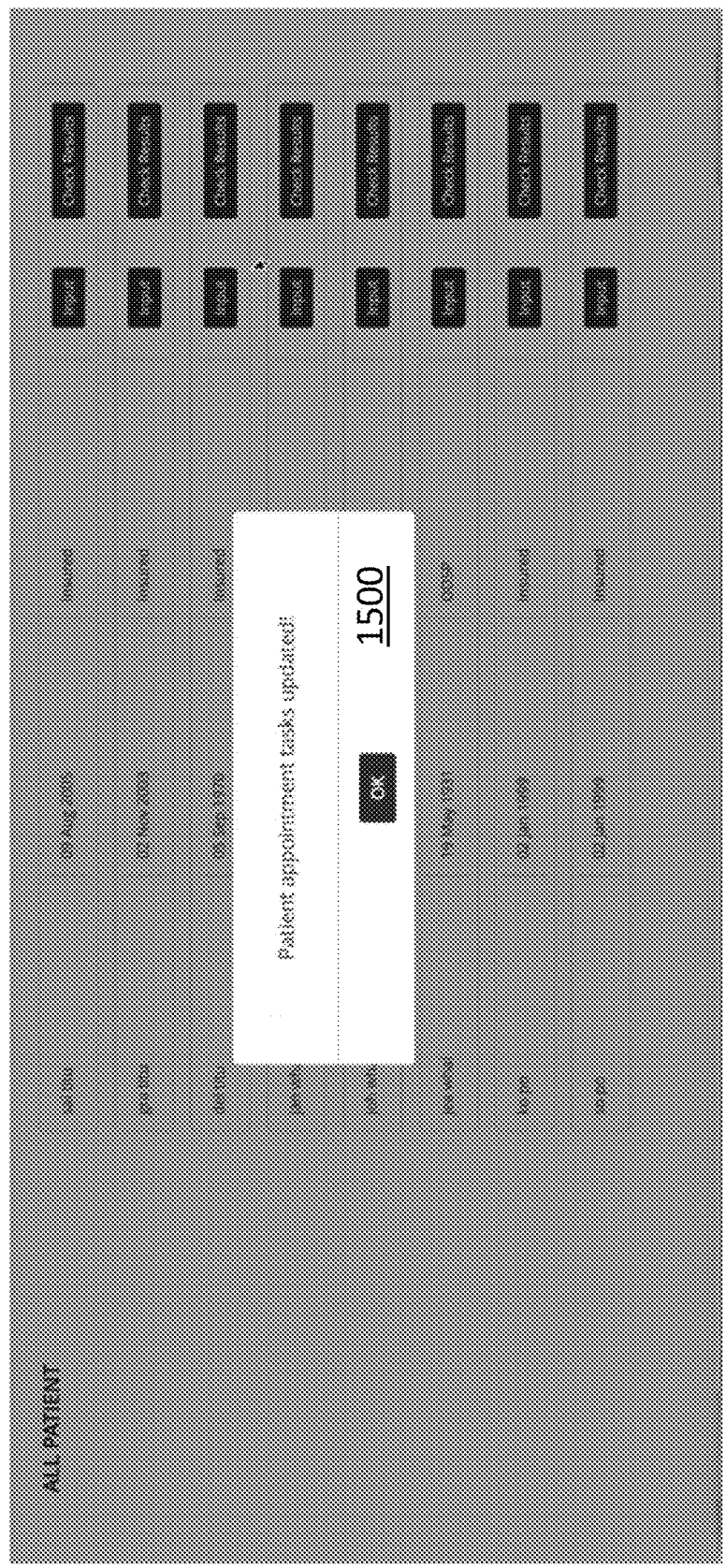
FIG. 15 depicts a confirmation message displayed after successful finalization of the selection of tasks or procedures for the first patient.

FIG. 15 depicts a confirmation message 1500 after successfully finalizing the selection of treatments or procedures to be performed for the patient during the appointment. In the example discussed with reference to FIG. 14, the appointment set of procedures satisfies the various criteria for determining a condition of being optimized and the Applicable Time does not exceed the total forty-minute Appointment time available, such that no conflict exists with either the preceding appointment (if applicable) or the subsequent appointment (if applicable). Thus, e.g., when the hygienist closes the form the confirmation message 1500 is displayed.

The dental hygienist preferably finalizes all of the appointments for the entire workday during the set-up procedure prior to the first appointment. Later, the hygienist accesses the previously generated appointment schedules at the time of each of the appointments and performs the treatments or procedures selected for each of the patients. Since the available treatments and procedures for each individual patient are presented to the dental hygienist in a way that facilitates rapid selection, and optionally provides feedback relating to the Applicable Time 1414 for completing the treatments and procedures compared to the available Appointment Time 1412, with additional feedback comparing the sum of the fees associated with the treatments and procedures, the hygienist is able to obtain an appointment set of procedures for every appointment during the day within the short amount of time allotted for reviewing the patient history. This avoids the problem of starting an appointment without selecting the treatments and procedures that are to be performed, which would then require the hygienist to spend time during the appointment deciding which treatments and procedures to perform.

Figure 16:
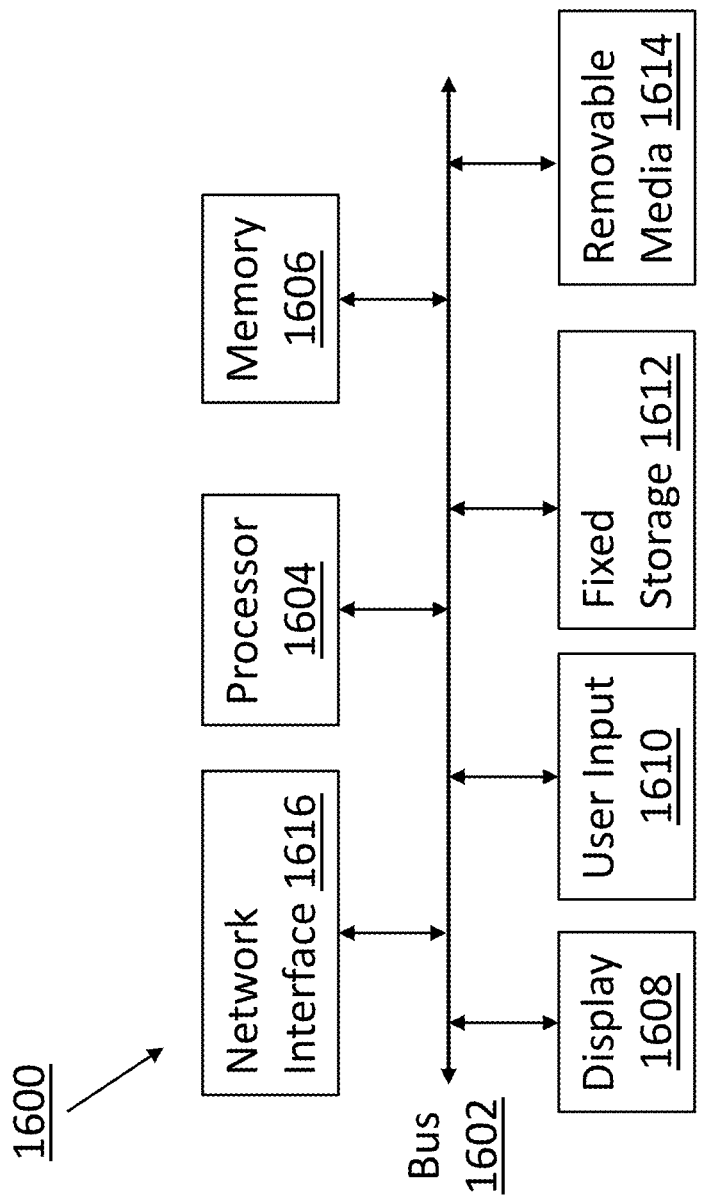
FIG. 16 shows a computer architecture suitable for implementation of embodiments.

Embodiments of the invention may be implemented in and used with a variety of component and network architectures. FIG. 16 is an example computing device 1600 suitable for implementing embodiments of the presently disclosed subject matter. The device 1600 may be, for example, a desktop or laptop computer, or a mobile computing device such as a smart phone, tablet, or the like. The device 1600 may include a bus 1602 which interconnects major components of the device 1600, such as a central processor 1604, a memory 1606 such as Random Access Memory (RAM), Read Only Memory (ROM), flash RAM, or the like, a user display 1608 such as a display screen, a user input interface 1610, which may include one or more controllers and associated user input devices such as a keyboard, mouse, touch screen, and the like, a fixed storage 1612 such as a hard drive, flash storage, and the like, a removable media component 1614 operative to control and receive an optical disk, flash drive, and the like, and a network interface 1616 operable to communicate with one or more remote devices via a suitable network connection.

The bus 1602 allows data communication between the central processor 1604 and one or more memory components, which may include RAM, ROM, and other memory, as previously noted. Typically, RAM is the main memory into which an operating system and application programs are loaded. A ROM or flash memory component can contain, among other code, the Basic Input-Output system (BIOS) which controls basic hardware operation such as the interaction with peripheral components. Applications resident with the device 1600 are generally stored on and accessed via a computer readable medium, such as a hard disk drive (e.g., fixed storage 1612), an optical drive, floppy disk, or other storage medium.

The fixed storage 1612 may be integral with the device 1600 or may be separate and accessed through other interfaces. The fixed storage device 1612 may include the data store 310 discussed above or may be in addition thereto. The network interface 1616 may provide a direct connection to a remote server via a wired or wireless connection. The network interface 1616 may provide such connection using any suitable technique and protocol as will be readily understood by one of skill in the art, including digital cellular telephone, WiFi, Bluetooth®, near-field, and the like. For example, the network interface 1616 may allow the device 1600 to communicate with other computers via one or more local, wide-area, or other communication networks, as described in further detail below.

Many other devices or components (not shown) may be connected in a similar manner (e.g., document scanners, digital cameras and so on). Conversely, all of the components shown in FIG. 16 need not be present to practice the present disclosure. The components can be interconnected in different ways from that shown. The operation of a device such as that shown in FIG. 16 is readily known in the art and is not discussed in detail in this application. Code to implement the present disclosure can be stored in computer-readable storage media such as one or more of the memory 1606, fixed storage 1612, removable media 1614, or on a remote storage location.

Figure 17:
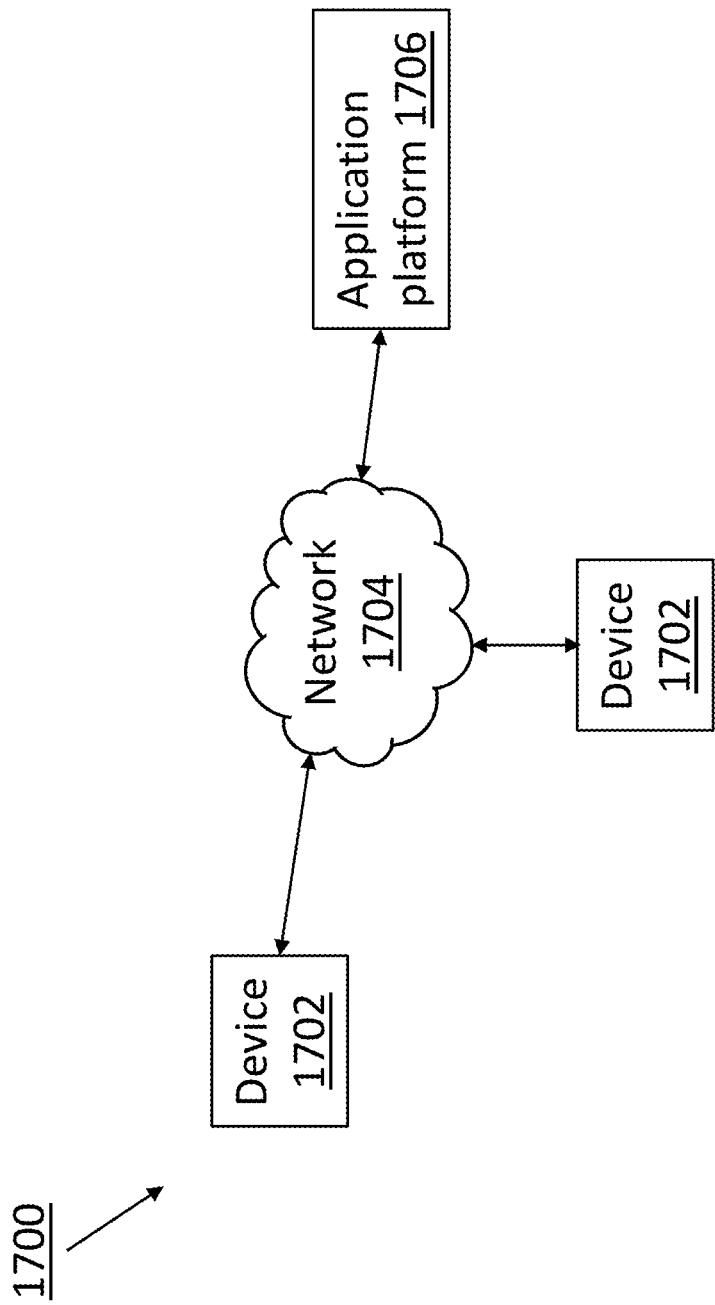
FIG. 17 shows an example distributed computing system suitable for implementation of embodiments.

FIG. 17 shows an example network arrangement 1700 suitable for implementing embodiments of the presently disclosed subject matter. One or more devices 1702, such as local computers, smart phones, tablet computing devices, and the like may connect to other devices via one or more networks 1704. Each device 1702 may be a computing device as previously described. The network may be a local network, wide-area network, the Internet, or any other suitable communication network or networks, and may be implemented on any suitable platform including wired and/or wireless networks. The devices may communicate with one or more remote devices, such as an application platform 1706. The application platform 1706 may include one or more servers and/or databases, as will be readily understood by one of skill in the art.

More generally, various embodiments of the presently disclosed subject matter may include or be embodied in the form of computer-implemented processes and apparatuses for practicing those processes. Embodiments also may be embodied in the form of a computer program product having computer program code containing instructions embodied in non-transitory and/or tangible media, such as floppy diskettes, CD-ROMs, hard drives, USB (universal serial bus) drives, or any other machine-readable storage medium, such that when the computer program code is loaded into and executed by a computer, the computer becomes an apparatus for practicing embodiments of the disclosed subject matter. Embodiments also may be embodied in the form of computer program code, for example, whether stored in a storage medium, loaded into and/or executed by a computer, or transmitted over some transmission medium, such as over electrical wiring or cabling, through fiber optics, or via electromagnetic radiation, such that when the computer program code is loaded into and executed by a computer, the computer becomes an apparatus for practicing embodiments of the disclosed subject matter. When implemented on a general-purpose microprocessor, the computer program code segments configure the microprocessor to create specific logic circuits.

In some configurations, a set of computer-readable instructions stored on a computer-readable storage medium may be implemented by a general-purpose processor, which may transform the general-purpose processor or a device containing the general-purpose processor into a special-purpose device configured to implement or carry out the instructions.

Embodiments may be implemented using hardware that may include a processor, such as a general-purpose microprocessor and/or an Application Specific Integrated Circuit (ASIC) that embodies all or part of the techniques according to embodiments of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to embodiments of the disclosed subject matter.

In the description of the invention herein, it is understood that a word appearing in the singular encompasses its plural counterpart, and a word appearing in the plural encompasses its singular counterpart, unless implicitly or explicitly understood or stated otherwise. For instance, unless the context indicates otherwise, a singular reference, such as "a" or "an" means "one or more". Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise. It is also to be understood, where appropriate, like reference numerals may refer to corresponding parts throughout the several views of the drawings for simplicity of understanding.

Throughout the description and claims of this specification, the words "comprise", "including", "having" and "contain" and variations of the words, for example "comprising" and "comprises" etc., mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

What is claimed is:

1. A computer implemented optimization method for automatically providing a set of dental procedures to be performed by a dental practitioner during a scheduled appointment, comprising:

accessing, by at least one processor, data stored in one or more storage devices, the data defining a first plurality of dental procedures, and the data further defining a billing rate associated with each dental procedure and a minimum allowable time associated with each dental procedure, wherein some dental procedures of the first plurality of dental procedures have different billing rates associated therewith;

determining, from the first plurality of dental procedures, a first list of dental procedures that are to be performed for a first patient during the scheduled appointment;

using the at least one processor, generating a second list of additional dental procedures that are available to be optionally performed for the same first patient during the same scheduled appointment, and ranking the additional dental procedures based on at least one of a monetary value contribution to a billing value of the appointment, a frequency of performing the additional dental procedures determined from profile data for the first patient, or a time-allocation requirement of a dental office limited resource; and using the at least one processor, automatically generating from the first list and from the second list an appointment set of procedures to optimize the billing value of the scheduled first appointment, and providing an output of the appointment set of procedures to the dental practitioner, wherein the appointment set of procedures generated is dependent upon the second list being different than a previous second list generated for the same first patient for a previous scheduled appointment, and wherein at least the minimum allowable time is allotted to each of the dental procedures within the appointment set of procedures.

2. The computer implemented optimization method of claim 1, wherein the first list of dental procedures consists of dental procedures that are performed for the first patient during every scheduled appointment.

3. The computer implemented optimization method of claim 2, wherein the first list of dental procedures is automatically populated by the at least one processor based on the first patient's first profile data relating to dental procedures performed during a plurality of previous scheduled appointments.

4. The computer implemented optimization method of claim 3, wherein the first list of dental procedures includes non-optional dental procedures that are populated by the at least one processor in a non-removable fashion.

5. The computer implemented optimization method of claim 1, wherein a total projected time required to perform all dental procedures of the appointment set of procedures matches a duration of the scheduled first appointment within a predetermined threshold range.

6. The computer implemented optimization method of claim 1, wherein a total projected time required to perform all dental procedures of the appointment set of procedures exceeds a duration of the scheduled first appointment, and wherein the dental procedures of the second list of additional dental procedures are ranked in order of monetary value contribution to the billing value of the appointment.

7. The computer implemented optimization method of claim 1, comprising, using the at least one processor, selecting from the stored first plurality of dental procedures a first subset of dental procedures that are available to be performed for the first patient during the scheduled first appointment in dependence upon the profile data for the first patient, wherein the first list of dental procedures and the second list of dental procedures include only those dental procedures of the first subset of dental procedures.

8. The computer implemented optimization method of claim 1, comprising comparing a total projected time required to perform all dental procedures of the first list of dental procedures and of the second list of dental procedures to a duration of the scheduled first appointment, and further comprising generating a new second list of dental procedures having a reduced time requirement relative to the initial second list of dental procedures.

9. The computer implemented optimization method of claim 8, comprising repeating the steps of comparing and of generating the new second list of dental procedures until the new second list of dental procedures results in a total projected time required to perform all dental procedures of the appointment set of procedures that matches a duration of the scheduled first appointment within a predetermined threshold range.

10. The computer implemented optimization method of claim 1, comprising changing at least one of a start time and an end time of the scheduled first appointment for the first patient if a total projected time required to perform all dental procedures of the appointment set of procedures does not match a duration of the scheduled first appointment within a predetermined threshold range.

11. The computer implemented optimization method of claim 1, wherein the appointment set of procedures is generated by the at least one processor in a fully automated fashion absent selection of the dental procedure by a human operator.

12. A system for automatically providing a dental practitioner with a set of dental procedures to be performed during a scheduled appointment, the system comprising:
one or more storage devices having stored therein data defining a first plurality of dental procedures, and the data further defining a billing rate associated with each dental procedure and a minimum allowable time associated with each dental procedure, wherein some dental procedures of the first plurality of dental procedures have different billing rates associated therewith
at least one processor in communication with the one or more storage devices, the at least one processor configured to:
determine, from the first plurality of dental procedures, a first list of dental procedures that are to be performed for a first patient during the scheduled appointment;
generate a second list of additional dental procedures that are available to be optionally performed for the same first patient during the same scheduled appointment, and rank the additional dental procedures based on at least one of a monetary value contribution to a billing value of the appointment, a frequency of performing the additional dental procedures determined from profile data for the first patient, or a time-allocation requirement of a dental office limited resource; and
automatically generate from the first list and from the second list an appointment set of procedures to optimize the billing value of the scheduled appointment, and provide an output of the appointment set of procedures to the dental practitioner,
wherein the appointment set of procedures generated is dependent upon the second list being different than a previous second list generated for the same first patient for a previous scheduled appointment, and
wherein at least the minimum allowable time is allotted to each of the dental procedures within the appointment set of procedures.

13. The computer implemented optimization method of claim 12, wherein the at least one processor is configured to automatically populate first list of dental procedures with dental procedures that are performed for the first patient during every scheduled appointment.

14. The computer implemented optimization method of claim 13, wherein the at least one processor is configured to automatically populate the first list of dental procedures based on the profile for the first patient relating to dental procedures performed during a plurality of previous scheduled appointments.

15. The computer implemented optimization method of claim 14, wherein the at least one processor is configured to automatically populate the first list of dental procedures with non-optional dental procedures in a non-removable fashion.

16. The computer implemented optimization method of claim 12, wherein a total projected time required to perform all dental procedures of the appointment set of procedures matches a duration of the scheduled first appointment within a predetermined threshold range.

17. The computer implemented optimization method of claim 12, wherein a total projected time required to perform all dental procedures of the appointment set of procedures exceeds a duration of the scheduled first appointment, and wherein the dental procedures of the second list of additional dental procedures are ranked in order of monetary value contribution to the billing value of the appointment.

18. The computer implemented optimization method of claim 12, wherein the at least one processor is configured to select, from the stored first plurality of dental procedures, a first subset of dental procedures that are available to be performed for the first patient during the scheduled first appointment in dependence upon the profile data for the first patient, and wherein the first list of dental procedures and the second list of dental procedures include only those dental procedures of the first subset of dental procedures.

19. The method of claim 12, wherein the at least one processor is configured to generate the appointment set of procedures in a fully automated fashion absent selection of the dental procedure by a human operator.

20. A non-transitory computer-readable medium storing a plurality of instructions which, when executed by a processor, perform a method for automatically providing a dental practitioner with a set of dental procedures to be performed during a scheduled appointment, the method comprising:
accessing, by at least one processor, data stored in one or more storage devices, the data defining a first plurality of dental procedures, and the data further defining a billing rate associated with each dental procedure and a minimum allowable time associated with each dental procedure, wherein some dental procedures of the first plurality of dental procedures have different billing rates associated therewith;
determining, from the first plurality of dental procedures, a first list of dental procedures that are to be performed for a first patient during the scheduled appointment;
using the at least one processor, generating a second list of additional dental procedures that are available to be optionally performed for the same first patient during the same scheduled first appointment, and ranking the additional dental procedures based on at least one of a monetary value contribution to a billing value of the appointment, a frequency of performing the additional dental procedures determined from profile data for the first patient, or a time-allocation requirement of a dental office limited resource; and
using the at least one processor, automatically generating from the first list and from the second list an appointment set of procedures to optimize the billing value of the scheduled appointment, and providing an output of the appointment set of procedures to the dental practitioner,
wherein the appointment set of procedures generated is dependent upon the second list being different than a previous second list generated for the same first patient for a previous scheduled appointment, and wherein at least the minimum allowable time is allotted to each of the dental procedures within the appointment set of procedures.

* * * * *